US008687819B2

(12) United States Patent
Künzle et al.

(10) Patent No.: US 8,687,819 B2
(45) Date of Patent: Apr. 1, 2014

(54) METHOD FOR MONITORING THE INFLUENCE OF AMBIENT NOISE ON STOCHASTIC GRADIENT ALGORITHMS DURING IDENTIFICATION OF LINEAR TIME-INVARIANT SYSTEMS

(75) Inventors: Bernhard Künzle, Berne (CH); Sarah Bostock, Berne (CH)

(73) Assignee: Bernafon AG, Berne (CH)

( * ) Notice: Subject to any disclaimer, the term of this patent is extended or adjusted under 35 U.S.C. 154(b) by 710 days.

(21) Appl. No.: 12/848,704

(22) Filed: Aug. 2, 2010

(65) Prior Publication Data

US 2011/0026725 A1 Feb. 3, 2011

Related U.S. Application Data

(60) Provisional application No. 61/230,954, filed on Aug. 3, 2009.

(30) Foreign Application Priority Data

Aug. 3, 2009 (EP) .................................... 09167076

(51) Int. Cl.
*A61F 11/06* (2006.01)

(52) U.S. Cl.
USPC ........................................................ 381/71.11

(58) Field of Classification Search
USPC ........... 381/71.11–71.14, 71.1–71.8, 93, 312, 381/320, 56, 58, 60, 314, 316, 330, 381/94.1–94.4, 317, 318
See application file for complete search history.

(56) References Cited

U.S. PATENT DOCUMENTS

| | | | |
|---|---|---|---|
| 4,689,818 | A | 8/1987 | Ammitzboll |
| 5,450,494 | A | 9/1995 | Okubo et al. |
| 5,680,467 | A | 10/1997 | Hansen |
| 5,999,631 | A | 12/1999 | Porayath et al. |

(Continued)

FOREIGN PATENT DOCUMENTS

| | | | | |
|---|---|---|---|---|
| EP | 2071873 A1 | 6/2009 | | |
| WO | WO 2008/000843 * | 1/2008 | ............. | H04R 25/00 |
| WO | WO 2008/000843 A2 | 1/2008 | | |

OTHER PUBLICATIONS

Dyrlund et al., "Acoustic feedback margin improvements in hearing instruments using a prototype DFS (digital feedback suppression) system", Scand Audiol, 20, pp. 49-53 (1991).

(Continued)

*Primary Examiner* — Lun-See Lao
(74) *Attorney, Agent, or Firm* — Birch, Stewart, Kolasch & Birch, LLP

(57) ABSTRACT

A hearing aid system and a method of estimating ambient noise in a listening device includes an input transducer and an output transducer, an electrical forward path between the input transducer and the output transducer providing a forward gain, an electrical feedback path comprising an adaptive filter for estimating the acoustic feedback gain from the output transducer to the input transducer. A method determines the quality of a critical gain measurement for a listening device. The method comprises a) monitoring the energy of the first-difference of the filter coefficients of the adaptive filter over time and b) applying a predefined threshold criterion to the change in energy content from one time instance to another to determine an acceptable impact of the ambient noise. This technique may e.g. be used for the fitting of hearing instruments where background noise is variable.

14 Claims, 2 Drawing Sheets

(56) References Cited

U.S. PATENT DOCUMENTS

| | | | | |
|---|---|---|---|---|
| 6,072,884 | A * | 6/2000 | Kates | 381/318 |
| 6,185,300 | B1 | 2/2001 | Romesburg | |
| 7,885,417 | B2 * | 2/2011 | Christoph | 381/71.11 |
| 2002/0176584 | A1 | 11/2002 | Kates | |
| 2005/0036632 | A1 | 2/2005 | Natarajan et al. | |

OTHER PUBLICATIONS

Engebretson et al., "Properties of an adaptive feedback equalization algorithm", J Rehabil Res Dev, vol. 30, No. 1, pp. 8-16 (1993).

Gunnarsson et al., "Frequency Domain Tracking Characteristics of Adaptive Algorithms," IEEE Trans. Acoustics, Speech and Sig. Proc., vol. 37, No. 7, pp. 1072-1089 (1989).

* cited by examiner

METHOD FOR MONITORING THE INFLUENCE OF AMBIENT NOISE ON STOCHASTIC GRADIENT ALGORITHMS DURING IDENTIFICATION OF LINEAR TIME-INVARIANT SYSTEMS

CROSS REFERENCE TO RELATED APPLICATIONS

This nonprovisional application claims the benefit under 35 U.S.C. 119(e) of U.S. Provisional Application No. 61/230,954 filed on Aug. 3, 2009 and under 35 U.S.C. 119(a) to Patent Application No. 09167076.0 filed in European Patent Office on Aug. 3, 2009. The entire contents of all of the above applications are hereby incorporated by reference into the present application.

TECHNICAL FIELD

The present invention relates to acoustic feedback cancellation, finding application in hearing aids and further audio devices. The invention relates specifically to a method of estimating an acoustic feedback path in a listening system, e.g. a hearing aid system. The invention relates in particular to a method of estimating the influence of ambient noise on an adaptive filter in steady state.

The invention furthermore relates to a hearing aid system, a computer readable medium and a data processing system.

The invention may e.g. be useful in applications where acoustic feedback is a problem, such as in the fitting of hearing instruments to a user's particular needs.

BACKGROUND ART

Frequency dependent acoustic, electrical and mechanical feedback identification methods are commonly used in hearing instruments to ensure their stability. Unstable systems due to acoustic feedback tend to significantly contaminate the desired audio input signal with narrow band frequency components, which are often perceived as howl or whistle.

It has been proposed that the stability of a system may be increased by specifically altering its transfer function at critical frequencies [Ammitzboll, 1987]. This can, for example, be achieved with a narrow frequency specific stop-band filter, referred to as a notch-filter [Porayath, 1999]. The disadvantage of this method is that gain has to be sacrificed at and around critical frequencies.

More advanced techniques suggest feedback cancellation by subtracting an estimate of the feedback signal within the hearing instrument. It has been proposed to use a fixed coefficient linear time invariant filter for the feedback path estimate [Dyrlund, 1991]. This method proves to be effective if the feedback path is steady state and, therefore, does not alter over time. However, the feedback path of a hearing aid does vary over time and some kind of tracking ability is often preferred.

Adaptive feedback cancellation has the ability to track feedback path changes over time. It is also based on a linear time invariant filter to estimate the feedback path but its filter weights are updated over time [Engebretson, 1993]. The filter update may be calculated using stochastic gradient algorithms, including some form of the popular Least Mean Square (LMS) or the Normalized LMS (NLMS) algorithms. They both have the property to minimize the error signal in the mean square sense with the NLMS additionally normalizing the filter update with respect to the squared Euclidean norm of some reference signal. A more advanced method combines stochastic gradient algorithms with statistical evaluation of the AFC filter coefficients over time and employs control circuitry in order to ensure the filter coefficients to be updated adequately in noisy situations [Hansen, 1997]. The statistical evaluation is sensible to changes of the phase response and magnitude-frequency response of the feedback path.

Applications like the fitting of a hearing aid require an estimate of the acoustic feedback path of each subject, in particular of the magnitude-frequency response of the acoustic feedback path. In an open-loop configuration, as illustrated in FIG. 1.*b*), an estimate of the feedback path may be obtained from the frequency response of the adaptive AFC filter (AFC=Adaptive Feedback Cancellation) after convergence of the NLMS algorithm. Background or ambient noise during the measurement influences the convergence behaviour of the NLMS algorithm, contaminates the final state of the AFC filter coefficients and, consequently, yields a distorted estimate of the acoustic feedback path. In order to alleviate this problem, it has been proposed to measure the undesired background noise directly at some defined input using Fourier Transform (FT) based methods. However, these methods require additional algorithms like the Fast Fourier Transform (FFT) and do not reflect the implications on the obtained AFC filter coefficients in a straight forward way.

DISCLOSURE OF INVENTION

The invention solving the impact evaluation of the background noise on the convergence of the NLMS and final adjustment involves the calculation of the first-difference of a time-series of the AFC filter coefficients. During and after convergence, the changes of the AFC filter coefficients are monitored for some time and used as a measure for the background noise.

In the present context, the first-difference of a time series is taken to mean the series of changes from one period to the next. It is a sequence of filter coefficients $h'(i,NT_s)$, $h'(i,2NT_s)$, . . . , $h'(i,(n-1)NT_s)$, $h'(i,nNT_s)$, $h'(i,(n+1)NT_s)$, . . . , taken at successive iterations n=1, 2, . . . in time $(nN)T_s$, where $T_s$ is a time step (a time step $T_s$ can e.g. correspond to the time between successive samples, i.e. $1/f_s$, where $f_s$ is the sampling frequency of an analogue to digital converter) and $N \in \mathbb{N}$ is a natural number. The first-difference $\Delta h'(n)$ of $h'(i,nNT_s)$ at iteration n, is defined as $\Delta h'(n)=h'(i,nNT_s)-h'(i,(n-1)NT_s)$, where each i=0, 1, 2, . . . , M represents one tab of the filter impulse response with order M.

An object of the present invention is to provide an alternative method of determining the quality of a feedback path measurement for an audio system, e.g. for a hearing instrument. Another object of the present invention is to provide an alternative method of determining the quality of the magnitude-frequency response of a feedback path measurement for an audio system, e.g. for a hearing instrument, while allowing the phase response of the feedback path to be altered during the measurement.

Objects of the invention are achieved by the invention described in the accompanying claims and as described in the following.

A Method of Estimating Ambient Noise:

An object of the invention is achieved by a method of estimating ambient noise in a listening system, the listening system comprising an input transducer for converting an input sound to an electrical input signal, including picking up an ambient noise, and an output transducer for converting an electrical output signal to an output sound, an electrical forward path being defined between the input transducer and the output transducer and providing a forward gain $|G(f)|$, f being frequency, the listening system further comprising an electrical feedback path comprising an adaptive filter for estimating an acoustic feedback gain $|H(f)|$ from the output transducer to the input transducer, the adaptive filter comprising a variable filter part and an algorithm part, the variable filter part providing an estimate of the acoustic feedback path based on filter coefficients $h'(i,nNT_s)$ determined by the algorithm part, where each i=0, 1, 2, . . . , M represents one tab of the impulse response with the filter order of M, $nNT_s$ being a time instance. The method comprises, a) monitoring the energy of the first-difference of the filter coefficients $h'(i,nNT_s)$ over time and b) applying a predefined threshold criterion to the change in energy content from one time instance to another to determine an acceptable impact of the ambient noise.

This has the advantage of providing a criterion which may be used to account for the impact of stationary and non-stationary background noise during the feedback path measurement.

In an embodiment, the variable filter part provides an estimate (only) of the magnitude-frequency response $|H(f)|$ of the acoustic feedback path. The above criterion has the advantage that it is resistant to changes of the phase response of the feedback path during the measurement.

The term 'estimating ambient noise' is intended to include deciding or detecting whether or not the ambient noise level is above or below a threshold level.

In a particular embodiment, the method comprises providing a probe signal, e.g. a broad-band noise-like signal, at a predefined initial level (i.e. a predefined magnitude and/or power density spectrum) and inserting said signal in the electrical forward path of the listening system. In an embodiment, the probe signal is inserted as an alternative to the normal input signal originating from the input transducer. This is termed a measurement mode. In an embodiment, a (possibly weighted) combination of the probe signal and the normal input signal originating from the input transducer is inserted in the forward path. In an embodiment, the probe signal is a white noise like signal with zero mean and variance r.

In a particular embodiment, the method comprises calculating $|\kappa_M(nNT_s)|$, the energy of the first-difference of the filter coefficients at two discrete successive time instances $nNT_s$ and $(n-1)NT_s$, where n represents one specific iteration, $T_s$ is a sampling period and $N \in N$ is a natural number.

In a particular embodiment, the method comprises that $|\kappa_M(nNT_s)|$, the energy of the first-difference of the filter coefficients, determined at two time instances $nNT_s$ and $(n-1)NT_s$, is determined by $$\kappa_M(nNT_s) \equiv \frac{1}{4}\sum_{i=0}^{M} |h'(i, nNT_s) - h'(i, (n-1)NT_s)|^2 \frac{\sum_{i=0}^{M} h'(i, nNT_s)^2 - \sum_{i=0}^{M} h'(i, (n-1)NT_s)^2}{\left|\sum_{i=0}^{M} h'(i, nNT_s)^2 - \sum_{i=0}^{M} h'(i, (n-1)NT_s)^2\right|}$$

where M is the order of the AFC filter $h'(i,nNT_s)$.

The first part of the expression for $\kappa_M(nNT_s)$ $$\frac{1}{4}\sum_{i=0}^{M} |h'(i, nNT_s)h'(i, (n-1)NT_s)|^2$$

represents the energy of the first-difference of the filter coefficients from one time unit to the next.

The second part $$\frac{\sum_{i=0}^{M} h'(i, nNT_s)^2 - h'(i, (n-1)NT_s)^2}{\left|\sum_{i=0}^{M} h'(i, nNT_s)^2 - h'(i, (n-1)NT_s)^2\right|}$$

represents the sign of the growth of the energy from one time instant to the next. For example, $\kappa_M(nNT_s)$ will be positive, if the energy of the first-difference from one time instant to the next one grows, and $\kappa_M(nNT_s)$ will be negative, if the energy is reduced.

In a particular embodiment, the method comprises that a threshold level $\kappa_T$ for $\kappa_M(nNT_s)$ may be based on approximated expressions for the mean square error [Gunnarsson, 1989], e.g. given by $$\kappa_T \equiv -\frac{\mu_0}{2\sum_{k=0}^{M} |U(k)|^2} \sum_{k=0}^{M} |V(k)|^2,$$

where $\mu_0$ is the step size parameter of the NLMS algorithm, V(k) a frequency domain representation (e.g. DFT(v(n)), where DFT is the Discrete Fourier Transform) of the input noise v(n) and U(k) a frequency domain representation (e.g. DFT(u(n)) of the output reference signal u(n) (cf. e.g. FIG. 1*b*). In an embodiment, the threshold criterion determines the boundary between an acceptable and an unacceptable level of ambient noise, $\kappa_M(nNT_s) \geq \kappa_T$ defining an acceptable level of ambient noise.

In an embodiment, a predefined minimum level of ambient noise is applied or ensured during measurement of the energy of the first-difference of the filter coefficients. In general, the noise may vary during the measurement. In an embodiment, the level of ambient noise is substantially constant during measurement of the energy of the first-difference of the filter coefficients.

According to the method of the present disclosure, the energy of the difference of the filter coefficients is sensible to changes of the magnitude response only, whereas the phase response is disregarded to a large extent, whereby the measurement is robust to changes of the phase response.

During fitting of a hearing aid to a particular user's needs, an audiologist makes measurements estimating the feedback path. In an embodiment, ambient noise is estimated according to the present method during such fitting, and the audiologist is informed, if too much background noise is present for a successful measurement to be performed, in which case he or she can perform another measurement.

A Method of Measuring Critical Gain in a Listening System:

In an aspect, a method of calculating critical gain in a listening system, e.g. a hearing instrument, is provided, the method using the method of estimating ambient noise described above, in the detailed description of 'mode(s) for carrying out the invention' and in the claims.

In an embodiment, the method comprises determining critical gain $G_{Critical}(f,nNT_s)=1/|H'(f,nNT_s)|$, where $H'(f,nNT_s)=FT(h'(i,nNT_s))$ represents an estimate of the transfer function of the actual acoustic feedback path $H(f,nNT_s)$ in the frequency-domain f. In an embodiment, the critical gain is determined according to the method during fitting of a hearing instrument to a particular user's needs, e.g. by an audiologist. In an embodiment, the critical gain measurements are performed separately for each frequency range or band.

A Computer-Readable Medium:

A tangible computer-readable medium storing a computer program is furthermore provided. The computer program comprises program code means for causing a data processing system to perform at least some (such as a majority or all) of the steps of the method described above, in the detailed description of 'mode(s) for carrying out the invention' and in the claims, when said computer program is executed on the data processing system.

A Data Processing System:

A data processing system is furthermore provided, the data processing system comprising a processor and program code means for causing the processor to perform at least some (such as a majority or all) of the steps of the method described above, in the detailed description of 'mode(s) for carrying out the invention' and in the claims.

A Listening System:

In an aspect, an object of the invention is achieved by A listening system comprising a listening device, the listening device comprising an input transducer for converting an input sound to an electrical input signal, including picking up an ambient noise, and an output transducer for converting an electrical output signal to an output sound, an electrical forward path being defined between the input transducer and the output transducer and comprising a signal processing unit providing a forward gain $|G(f)|$, f being frequency, the listening device further comprising an electrical feedback path comprising an adaptive filter for estimating the acoustic feedback gain $|H(f)|$ from the output transducer to the input transducer, the adaptive filter comprising a variable filter part and an algorithm part, the variable filter part providing an estimate of the acoustic feedback path based on filter coefficients $h'(i,nNT_s)$ determined by the algorithm part, where each i=0, 1, 2, . . . , M represents one tab of the filter impulse response with order M at time instance $nNT_s$ at measurement iteration n, wherein the signal processing unit is adapted for monitoring the energy content of the filter coefficients $h'(i,nNT_s)$ over time and to detect whether the change in energy content from one time instance to another exceeds a predefined threshold criterion to determine an acceptable level of the ambient noise.

It is intended that the process features of the method described above, in the detailed description of 'mode(s) for carrying out the invention' and in the claims can be combined with the system, when appropriately substituted by corresponding structural features and vice versa. Embodiments of the system have the same advantages as the corresponding method.

In an embodiment, the variable filter part is adapted to provide an estimate of the magnitude-frequency response $|H(f)|$ of the acoustic feedback path H(f). In an embodiment, the phase-response angle (H(f)) of the acoustic feedback path is not used for determining the threshold criterion.

In an embodiment, the listening system comprises a probe signal generator, e.g. a noise generator for generating a broad-band noise-like stimuli signal at a predefined initial level and a selector for selecting either the normal input based on the electric input signal or the noise stimuli signal based on a mode input and for inserting the output of said selector in the electrical forward path of the listening device, e.g. a hearing instrument, e.g. for use as an input to the signal processing unit. In an embodiment, the selector has at least two inputs and one output. In an embodiment, the output of the selector is one of the inputs. In an embodiment, the output of the selector is a weighted mixture of two or more of the inputs. In an embodiment, the output of the selector represents the signal of the electrical forward path at that location of the forward path (i.e. where the output signal fed to the output transducer originates from (is based on) the output of the selector). In an embodiment, the probe signal generator is adapted to provide a broad-band noise-like signal. In an embodiment, the probe signal generator is adapted to provide a white noise signal.

In a particular embodiment, the listening system is adapted to be, respectively, in a normal mode, wherein the normal input based on the electric input signal is used to generate the output signal fed to the output transducer, and in a measurement mode where the signal from the probe signal generator is used to generate the output signal fed to the output transducer.

In an embodiment, the listening system comprises a hearing aid system. In an embodiment, a listening device comprises a hearing instrument, a headset, a mobile telephone. In an embodiment, the listening system comprise a public address system, e.g. a karaoke system, or any other audio system where acoustic feedback (e.g. from a speaker to a microphone) may be a problem.

Use:

Use of a listening system as described above, in the detailed description of 'mode(s) for carrying out the invention' and in the claims is furthermore provided. In an embodiment, use of a listening system during fitting of a hearing instrument is provided.

Further objects of the invention are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The invention will be explained more fully below in connection with a preferred embodiment and with reference to the drawings in which.

The figures are schematic and simplified for clarity, and they just show details which are essential to the understanding of the invention, while other details are left out.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

MODE(S) FOR CARRYING OUT THE INVENTION

Figure 1A:
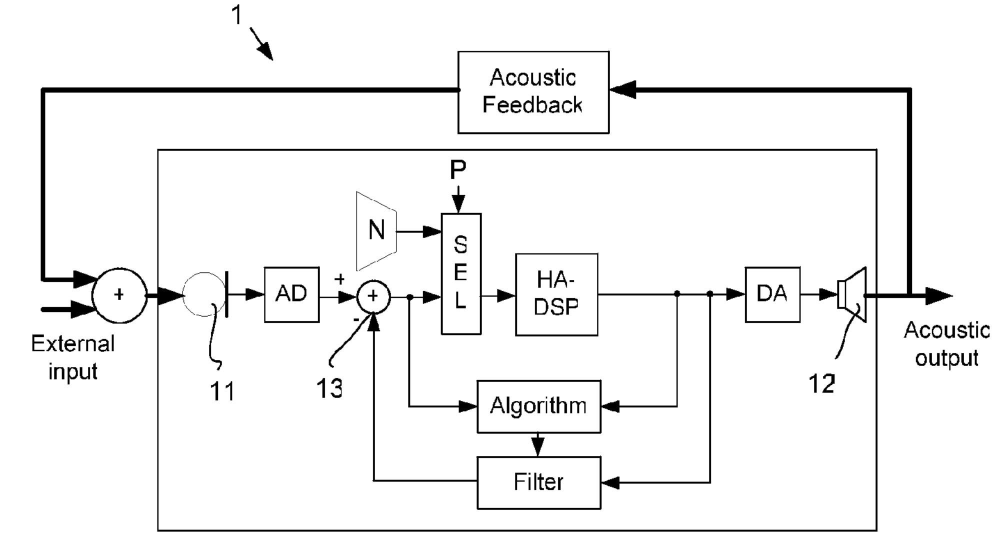
FIG. 1 shows a hearing instrument according to an embodiment of the invention (FIG. 1*a*) and an AFC system of a hearing instrument and its surrounding functional blocks suitable for carrying out an embodiment of a method according to the invention (FIG. 1*b*)

FIG. 1*a* shows some of the functional blocks of a hearing aid system 1, comprising a forward path and an (unintentional) acoustical feedback path of a hearing aid. In the present embodiment, the forward path comprises an input transducer 11 for receiving an external acoustic input from the environment, an AD-converter, a selector SEL for selecting as an output one of two input signals (alternatively a mixer providing a weighted combination of two input signals, may be used), a processing part HA-DSP for adapting the signal to the needs of a wearer of the hearing aid, a DA-converter (optional) and an output transducer 12 for generating an acoustic output to a wearer of the hearing aid. The intentional forward or signal path and components of the hearing aid are enclosed by the solid outline. An (external, unintentional) acoustical feedback path Acoustic Feedback from the output transducer to the input transducer is indicated. The acoustic input signal to the microphone 11 is a sum of an acoustic feedback signal and an external acoustic input signal (symbolically added by SUM-unit '+' preceding the microphone 11). The external acoustic input signal includes background or ambient noise. The hearing aid system additionally comprises an electrical feedback cancellation path for reducing or cancelling acoustic feedback from the 'external' feedback path from output to input transducer of the hearing aid (termed 'Acoustic Feedback' in FIG. 1*a*, the 'external' acoustic feedback path estimated by the electrical feedback cancellation path here including microphone and AD-converter and DA-converter and receiver). Here, the electrical feedback cancellation path comprises an adaptive filter, which is controlled by a prediction error algorithm, e.g. a NLMS like algorithm, in order to predict and cancel the part of the microphone signal that is caused by feedback from the receiver to the microphone of the hearing aid. The adaptive filter (in FIG. 1*a* comprising a 'Filter' part and a prediction error 'Algorithm' part) is aimed at providing a good estimate of the 'external feedback path' from the input of the DA to the output from the AD. The prediction error algorithm uses a reference signal together with the (feedback corrected) microphone signal to find the setting of the adaptive filter that minimizes the prediction error when the reference signal is applied to the adaptive filter. The forward path of the hearing aid comprises signal processing (termed 'HA-DSP' in FIG. 1*a*) to adjust the signal to the (possibly impaired) hearing of the user. In the embodiment of FIG. 1*a*, the processed output signal from the signal processing unit (HA-DSP) is used as the reference signal, which is fed to (the Algorithm and Filter parts of) the adaptive filter. The selector (SEL) receives as inputs 1) the feedback corrected input signal (output of summation unit 13) and 2) the output of a probe noise generator (N) (e.g. a white noise generator). In a normal mode (e.g. selected by the mode select parameter P=1) the feedback corrected input signal is selected and fed to the signal processing unit. In a fitting mode (e.g. selected by the mode select parameter P=0), where critical gain is measured, the output of the probe noise generator is selected and fed to the signal processing unit. In an embodiment, the two input signals are both fed to the signal processing unit, so that the measurement can be performed using the combined signal (e.g. a weighted combination, the weights being e.g. controlled by control input(s) P, the weights being e.g. in the range from 0.2 to 0.8).

Figure 1B:
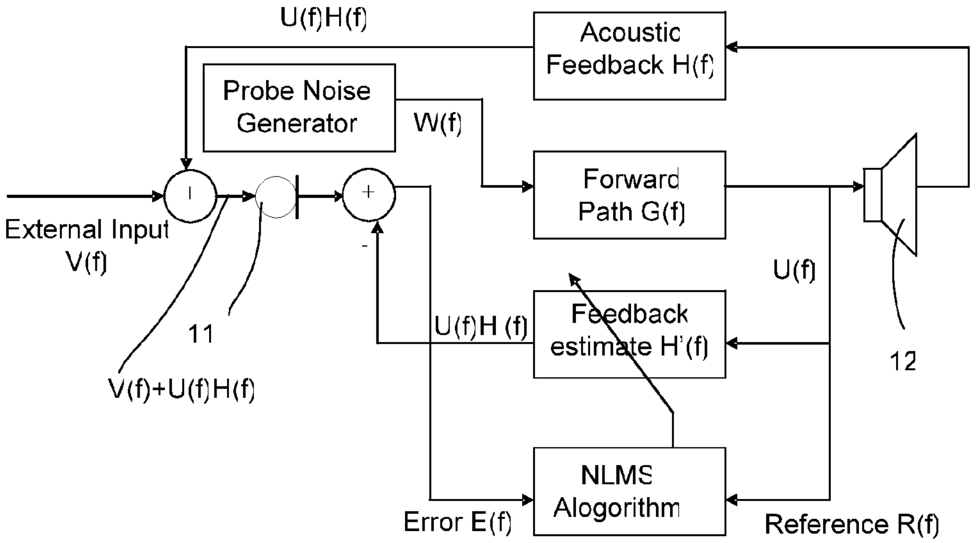

The signals of FIG. 1*b* are generally shown to be dependent on the frequency f. In practice this implies the existence of time to frequency conversion and frequency to time conversion units (e.g. in connection with the input 11 and output 12 transducers, respectively). Such conversion units may be implemented in any convenient way, including filter banks, Fourier Transformation (FT, e.g. Discrete FT (DFT) or Fast FT (FFT)), time-frequency mapping, etc.

The evaluation and impact of the background or ambient noise is crucial for several hearing instrument applications. For example, it may be required to measure critical gain $G_{Critical}(f)=1/H(f)$, where H(f) represents the transfer function of the Acoustic Feedback path in the frequency-domain f. The Acoustic Feedback path H(f) is estimated using an internal Noise Generator providing a broad-band noise-like signal W(f) and an adaptive filter comprising filter part Feedback estimate H'(f) and algorithm part NLMS Algorithm as illustrated in FIG. 1*b*. The NLMS algorithm of FIG. 1*b* together with the filter H'(f) provides an estimate of the feedback path H(f). The probe noise signal W(f) (e.g. a white noise signal) is fed to the forward path gain unit Forward Path G(f), whose output U(f)=W(f)G(f)) is fed to output transducer 12 for being presented to a user. The output U(f) is further used as a reference signal (also termed Reference R(f) in FIG. 1*b*) to the adaptive filter and fed to the filter as well as the algorithm parts of the adaptive filter. The output signal from output transducer 12 is filtered through the Acoustic Feedback H(f) path and the output thereof is added with an External Input V(f) in SUM unit '+', the combined signal being picked up by the input transducer 11. The External Input V(f) represents other acoustic signals (e.g. ambient noise) than the acoustic feedback signal. The electrical output (=V(f)+U(f)H(f)) of input transducer 11 is fed to a SUM unit '+' wherein an estimate of the acoustic feedback (output of filter part Feedback Estimate H'(f) of the adaptive filter) is subtracted. The resulting output (E(f)=V(f)+U(f)[H(f)−H'(f)]) of the SUM unit is the feedback corrected input signal, termed the error signal (Error E(f) in FIG. 1*b*), and is fed to the algorithm part (here NLMS Algorithm) of the adaptive filter. The noise generator (Probe Noise Generator) located within the hearing instrument creates e.g. a broad-band noise-like signal W(f) with a magnitude frequency spectrum of close to unity $|W(f)|=1$, for $f_{min} \le f \le f_{max}$ (the magnitude of a complex number X being indicated as |X|). A broad-band noise-like signal is in the present context taken to mean a signal with a substantially flat power spectral density (in the meaning that the signal contains substantially equal power within a fixed bandwidth when said fixed bandwidth is moved over the frequency range of interest $f_{min} \le f \le f_{max}$, e.g. a part of the human audible frequency range 20 Hz-20 kHz; in practice over the frequency range over which the instrument is designed to process an input signal, e.g. from 20 Hz to 8 kHz or to 12 kHz). With this setup the NLMS algorithm converges to $H'(f) \approx H(f)$. A common measure of the accuracy of the Feedback estimate H'(f) at some time instance $nNT_s$ is the Mean Square Error (MSE)

$$\hat{\pi}(f,nNT_s)=E|H'(f,nNT_s)-H(f,nNT_s)|^2,$$

where E is the expected value operator and $|\cdot|^2$ denotes magnitude squared of a generally complex argument '·'. The MSE strongly depends on the disturbing noise that is present during the measurement. Consequently, it is advantageous to have some background noise evaluation or monitoring going on while the measurement is running. Also, $\hat{\pi}(f,nNT_s)$ can not be calculated during runtime as the actual feedback path H(f, $nNT_s$) is unknown.

Basic Idea for Monitoring the Influence of Ambient Noise on the Convergence of the Adaptive Filter:

The basic idea is to monitor the ambient (background) noise indirectly by monitoring the energy of the first-difference of the filter coefficients $h'(i,nNT_s)=IFT(H'(f,nNT_s))$ over time (IFT=Inverse Fourier Transform). This is done by reading the filter coefficients $h'(i,nNT_s)$ and calculating $|\kappa_M(nNT_s)|$, the energy of the first-difference of the filter coefficients $h'(i,nNT_s)$ at each temporal iteration $nNT_s$:

$$\kappa_M(nNT_s) \equiv \frac{1}{4}\sum_{i=0}^{M}|h'(i,nNT_s)-h'(i,(n-1)NT_s)|^2$$

$$\frac{\sum_{i=0}^{M}h'(i,nNT_s)^2-\sum_{i=0}^{M}h'(i,(n-1)NT_s)^2}{\left|\sum_{i=0}^{M}h'(i,nNT_s)^2-\sum_{i=0}^{M}h'(i,(n-1)NT_s)^2\right|}$$

where $h'(i,nNT_s)$, i=0, 1, 2, . . . , M is the impulse response with order M of the adaptive FIR Filter with the frequency response $H'(f,nNT_s)$, estimating the actual acoustic feedback path H(f). Assuming H(f) to be steady state during the measurement, it can be shown for the NLMS algorithm that, after convergence, $\hat{\pi}(f,nNT_s)|_{n\to\infty}$ depends on the background noise v(n), the reference signal u(n) and the step size parameter $\mu_0$ by $$\hat{\pi}(f,nNT_s)\approx\frac{\mu_0}{2\sum_{k=0}^{M}|U(k)|^2}\sum_{k=0}^{M}|V(k)|^2$$

where V(k)=DFT(v(n)) and U(k)=DFT(u(n)) (DFT=Discrete Fourier Transform). The time difference between each measurement $t_{pause}=NT_s$ can e.g. be ≤5 s, such as ≤3 s, such as ≤2 s, such as in the range between 1 s and 2 s. Therefore, the determination of the background noise is obtained by comparing $\kappa_M(nNT_s)$ with some predefined threshold $\kappa_T$. As long as $\kappa_M(nNT_s)$ is above the chosen threshold $\kappa_T$, the ambient noise is considered to be negligible.

EXAMPLE

Measurement of Critical Gain During Fitting

Consider a threshold level $\kappa_T$ for the case U(k)=V(k), k=0, 1, 2, . . . , M, given by $$\kappa_T\equiv\frac{\mu_0}{2}$$

And the initial condition: Filter coefficients $h'(i,nNT_s=0)=0$. That is, the AFC filter coefficients are preferably set to zero at the beginning of the measurement. An example of an initial step size $\mu_0$ is 1/32.

To reliably detect a border between an acceptable and an unacceptable amount of ambient noise, the feedback path is considered to be steady state during the measurement procedure.

Figure 2:
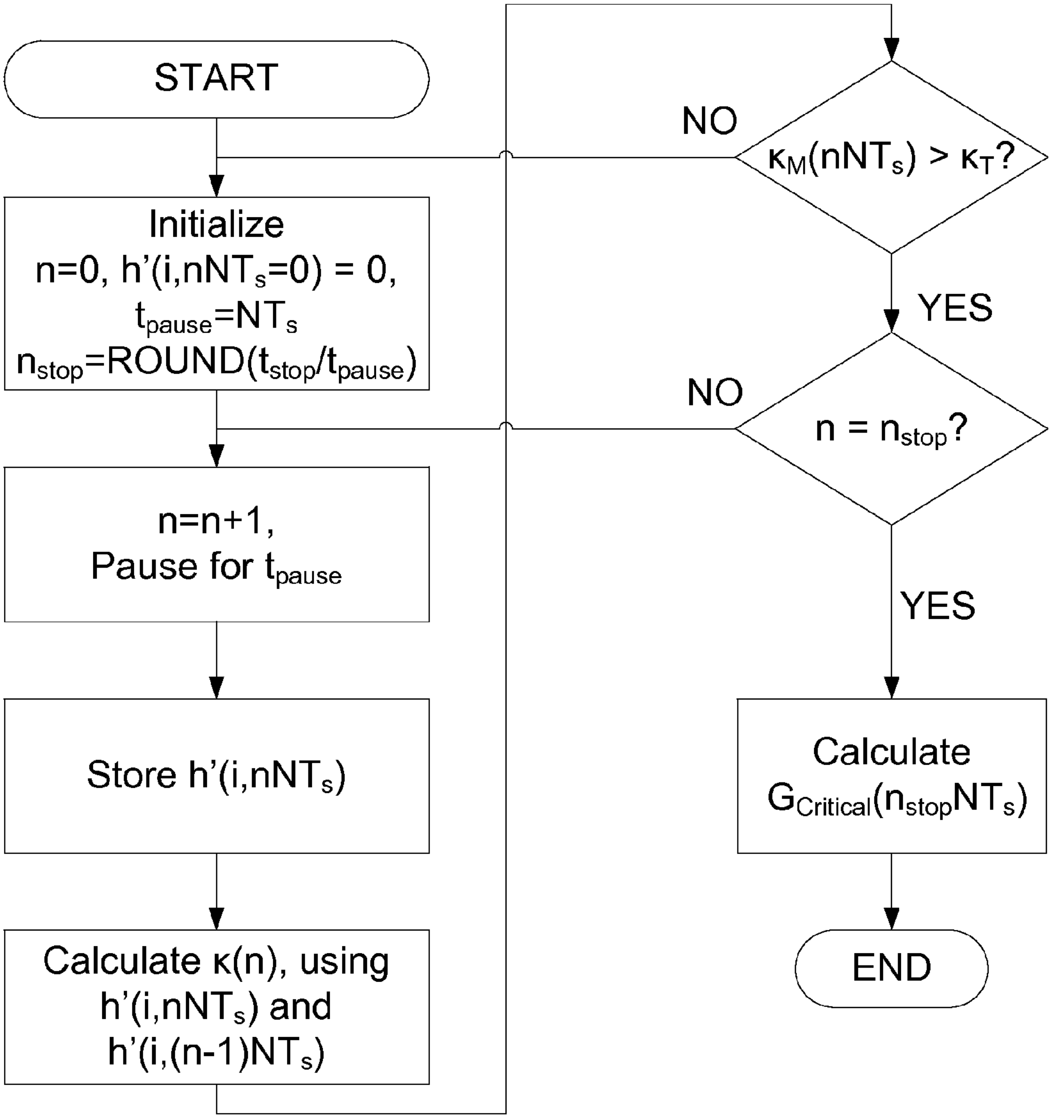
FIG. 2 shows a flowchart of an embodiment of a method according to the invention.

Measurement Procedure:

FIG. 2 shows an algorithm for measuring critical gain in a hearing instrument. In an embodiment, the algorithm comprises the following steps (which are correspondingly illustrated in FIG. 2):

0. Start: Set $n=n_{start}0$. Initialize filter coefficients $h'(i,nNT_s=0)=0$. Store ambient noise threshold level $\kappa_T$. Set stop at iteration $n_{stop}=ROUND(t_{stop}/t_{pause})$, where $t_{pause}=NT_s$, $T_s$ is the sampling period and N∈N (integer). Set step size $\mu_0$ of the NLMS algorithm. Set $t_{pause}$ with time step parameter N.
1. Let time $t_{pause}$ pass until, $t=(n+1)NT_s=nNT_s+NT_s$.
2. Store the filter coefficients $h'(i,nNT_s)$.
3. Read the filter coefficients $h'(i,nNT_s)$ and calculate $\kappa_M(nNT_s)$, using also previously stored filter coefficients $h'(i,(n-1)NT_s)$.
4. Check for ambient noise
   - If $(\kappa_M(nNT_s)>\kappa_T)$, Measurement is running smoothly; Continue;
   - Else, too much ambient noise is present, measurement failed (quit procedure or restart with some smaller step size parameter, e.g. $\mu_0-\Delta\mu_0$); restart procedure from step 0;
   - If iteration $n=n_{stop}$, calculate critical gain $G_{Critical}(n_{stop}NT_s)$; Measurement succeeded. Go to step 5;
   - Else, continue from step 1;
5. End In an embodiment $T_s$=50 μs corresponding to a sampling frequency $f_s$ of 20 kHz. In an embodiment, N=20000, leading to $t_{pause}$=NT=1 s.

In an embodiment, $t_{pause}$ is e.g. ≥1 s, such as ≥2 s, such as ≥5 s.

In an embodiment, the last iteration $n_{stop}$ corresponds to a time $t_{stop}=n_{stop}t_{pause}$≥2 s, such as ≥15 s, such as ≥30 s.

In an embodiment, $\Delta\mu_0=0.5\cdot\mu_0$. This is an so it is an example of a reduction in step size, which can be used when too much ambient noise is present, so that a measurement fails and the procedure has to restart with a smaller step size parameter $\mu_0-\Delta\mu_0$.

Typically, the threshold $\kappa_T$ is independent on the signal type. In particular embodiments, however, different threshold levels $\kappa_T$ are defined for different types of signals.

The critical gain $G_{Critical}(f, n_{stop}t_{pause})$ is estimated by 1/H'(f, $n_{stop}t_{pause}$).

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims. Although the above examples of embodiments of the invention are in related to hearing aids, other fields of application where acoustic feedback may pose problems, including public address systems, can be envisaged.

REFERENCES

[Ammitzboll, 1987] U.S. Pat. No. 4,689,818, "Resonant peak control", 1987

[Porayath, 1999] U.S. Pat. No. 5,999,631 "Acoustic feedback elimination using adaptive notch filter algorithm", 1999

[Dyrlund, 1991] O. Dyrlund, N. Bisgaard, "Acoustic feedback margin improvements in hearing instruments using a prototype DFS (digital feedback suppression) system", Scand Audiol, 20(1), pp. 49-53, 1991

[Engebretson, 1993] A. Engebretson, M. French-St. George, "Properties of an adaptive feedback equalization algorithm", J Rehabil Res Dev, 30(1), pp. 8-16, 1993

[Hansen, 1997] U.S. Pat. No. 5,680,467, "Hearing Aid Compensating for Acoustic Feedback", 1997

[Gunnarsson, 1989] S. Gunnarsson, L. Ljung, "Frequency Domain Tracking Characteristics of Adaptive Algorithms," IEEE Trans. Acoustics, Speech and Sig. Proc., Vol. 37, No. 7, pp. 1072-1089, 1989

The invention claimed is:

1. A method of estimating ambient noise in a listening system, the listening system comprising an input transducer for converting an input sound to an electrical input signal, including picking up an ambient noise, and an output transducer for converting an electrical output signal to an output sound, an electrical forward path being defined between the input transducer and the output transducer and providing a forward gain $|G(f)|$, f being frequency, the listening system further comprising an electrical feedback path comprising an adaptive filter for estimating an acoustic feedback gain $|H(f)|$ from the output transducer to the input transducer, the adaptive filter comprising a variable filter part and an algorithm part, the variable filter part providing an estimate of the acoustic feedback path based on filter coefficients $h'(i,nNT_s)$ determined by the algorithm part, where each $i=0, 1, 2, \ldots, M$ represents one tab of the impulse response with the filter order of M at the specific instance in time $nNT_s$ at the measurement iteration n, the method comprising a) monitoring an energy $\kappa_M(nNT_s)$ of a first-difference of the filter coefficients $h'(i,nNT_s)$ over time; and b) applying a predefined threshold criterion to the change in energy content from one time instance to another to determine an acceptable impact of the ambient noise, wherein the energy $\kappa_M(nNT_s)$ of the first-difference of the filter coefficients over time is calculated at a time instance $nNT_s$, where $T_s$ is a sampling period, N is an integer, and $$\kappa_M(nNT_s) \equiv \frac{1}{4}\sum_{i=0}^{M} \left| h'(i, nNT_s) - h'(i, (n-1)NT_s)\right|^2 \frac{\sum_{i=0}^{M} h'(i, nNT_s)^2 - \sum_{i=0}^{M} h'(i, (n-1)NT_s)^2}{\left|\sum_{i=0}^{M} h'(i, nNT_s)^2 - \sum_{i=0}^{M} h'(i, (n-1)NT_s)^2\right|},$$

where M is the order of the AFC filter $h'(i,nNT_s)$.

2. A method according to claim 1 comprising providing a broad-band noise-like signal at a predefined initial level and inserting the said signal in the electrical forward path of the listening system.

3. A method according to claim 1 wherein a threshold criterion $\kappa_T$ for $\kappa_M(nNT_s)$ is given by $$\kappa_T \equiv -\frac{\mu_0}{2\sum_{k=0}^{M}|U(k)|^2}\sum_{k=0}^{M}|V(k)|^2,$$

where $\mu_0$ is the step size parameter,

V(k) is a frequency representation of the input noise v(n) and

U(k)=DFT(u(n)) is a frequency representation of the output reference signal u(n), and where the threshold criterion determines the boundary between an acceptable and an unacceptable level of ambient noise, $\kappa_M(nNT_s) \geq \kappa_T$ defining an acceptable level of ambient noise.

4. A method according to claim 1 wherein the filter coefficients at iteration n=0, $h'(i,nNT_s=0)=0$.

5. A method according to claim 1 wherein the level of the white noise signal is increased, if the level of ambient noise is detected to be larger than a threshold level.

6. A method according to claim 1 wherein the variable filter part provides an estimate of the magnitude-frequency response $|H(f)|$ of the acoustic feedback path, while being resistant to changes of the phase-response angle (H(f)).

7. A method of calculating critical gain in a listening system using the method of estimating ambient noise according to claim 1.

8. A method of calculating critical gain according to claim 7 comprising determining critical gain $G_{Critical}(f)=1/|H'(f,n_{stop}NT_s)|$, where H'(f) represents an estimate of the transfer function of the acoustic feedback path in the frequency-domain f.

9. A non-transitory tangible computer-readable medium storing a computer program comprising program code means for causing a data processing system to perform the steps of the method of claim 1, when said computer program is executed on the data processing system.

10. A data processing system comprising a processor and program code means for causing the processor to perform the steps of the method of claim 1.

11. A listening system, comprising:

a listening device, the listening device comprising an input transducer for converting an input sound to an electrical input signal, including picking up an ambient noise, and an output transducer for converting an electrical output signal to an output sound, an electrical forward path being defined between the input transducer and the output transducer, the electrical forward path comprising a signal processing unit providing a forward gain $|G(f)|$, f being frequency, the listening device further comprising an electrical feedback path comprising an adaptive filter for estimating the acoustic feedback gain $|H(f)|$ from the output transducer to the input transducer, the adaptive filter comprising a variable filter part and an algorithm part, the variable filter part providing an estimate of the acoustic feedback path based on filter coefficients $h'(i,nNT_s)$ determined by the algorithm part, where each i=0, 1, 2, . . . M represents one tab of the filter impulse response with order M at time instance $nNT_s$ at measurement iteration n, wherein the signal processing unit is configured to monitor an energy $\kappa_M(nNT_s)$ of a first-difference of the filter coefficients $h'(i,nNT_s)$ over time and to detect whether the change in energy content from one time instance to another exceeds a predefined threshold criterion to determine an acceptable level of the ambient noise, wherein the energy $\kappa_M(nNT_s)$ of the first-difference of the filter coefficients over time is calculated at a time instance $nNT_s$, where $T_s$ is a sampling period, N is an integer, and $$\kappa_M(nNT_s) \equiv \frac{1}{4}\sum_{i=0}^{M} |h'(i, nNT_s) - h'(i, (n-1)NT_s)|^2 \frac{\sum_{i=0}^{M} h'(i, nNT_s)^2 - \sum_{i=0}^{M} h'(i, (n-1)NT_s)^2}{\left|\sum_{i=0}^{M} h'(i, nNT_s)^2 - \sum_{i=0}^{M} h'(i, (n-1)NT_s)^2\right|},$$

-continued where M is the order of the AFC filter $h'(i,nNT_s)$.

12. A listening system according to claim 11, further comprising:

a white noise generator for generating a white noise signal at a predefined initial level; and a selector for selecting either a normal input based on the electric input signal or the white noise signal based on a mode input and for inserting the output of said selector in the electrical forward path of the listening device.

13. A listening system according to claim 11 wherein the listening device comprises a hearing instrument, a headset or a mobile telephone.

14. A listening system according to claim 11, wherein the variable filter part is adapted to provide an estimate of the magnitude-frequency response |H(f)| of the acoustic feedback path.

* * * * *